United States Patent [19]

Averett, Jr.

[11] 4,163,292
[45] Aug. 7, 1979

[54] HIP PROSTHESIS

[76] Inventor: James E. Averett, Jr., 3612 Castlegate Dr., NW., Atlanta, Ga. 30327

[21] Appl. No.: 853,451

[22] Filed: Nov. 21, 1977

[51] Int. Cl.² ............................................. A61F 1/24
[52] U.S. Cl. .................................. 3/1.913; 128/92 CA
[58] Field of Search .................................. 3/1.9–1.913; 128/92 CA, 92 C

[56] References Cited

U.S. PATENT DOCUMENTS

| 3,795,922 | 3/1974 | Herbert et al. | 3/1.911 |
| 3,843,975 | 10/1974 | Tronzo | 3/1.913 |

FOREIGN PATENT DOCUMENTS 1506594  11/1967  France ................................... 128/92 C

OTHER PUBLICATIONS

"Functional Results of Hip Arthroplasty with Acrylic Prosthesis" by Merle d'Aubigne et al., The Journal of Bone & Joint Surgery, vol. 36-A, No. 3, Jun. 1954, pp. 451–475.
4013 Moore Head-Neck Prostheses in Zimaloy, Zimmer Catalog, Warsaw, Ind., p. A20, Feb. 1973.
Moore Hip Prostheses (4021, 4022, 4023), p. A18, rev. 1 (Feb. 1973), 30-4022 Solid Regular Straight Stem, 30-4023 Solid Narrow Straight Stem Moore Hip Prosthesis, p. A18-1, rev. 2, (Jan. 1974), Zimmer Catalog, Warsaw, Ind.

Primary Examiner—Ronald L. Frinks
Attorney, Agent, or Firm—Newton, Hopkins & Ormsby

[57] ABSTRACT

A prosthesis for the primary replacement of intertrochanteric fracture fragments to prevent the multitude of complications resulting from open reduction and nailing of intertrochanteric fractures. The prosthesis replaces the femoral head, neck and comminuted trochanteric portion including the lesser trochanter. The shaft of the femur is cut to form a square notch for prosthetic insertion and seating with the base of this notch approximately at the level of the inferior border of the lesser trochanter. When a proper fit has been accomplished the prosthesis is cemented into the femoral shaft and is then reduced into the acetabulum. When the greater trochanteric fragment is fractured transversely, it can be repositioned and held with wire secured through the holes in the prosthesis. The treatment is particularly useful with elderly patients since weight bearing can take place almost immediately followed by early ambulation.

5 Claims, 6 Drawing Figures

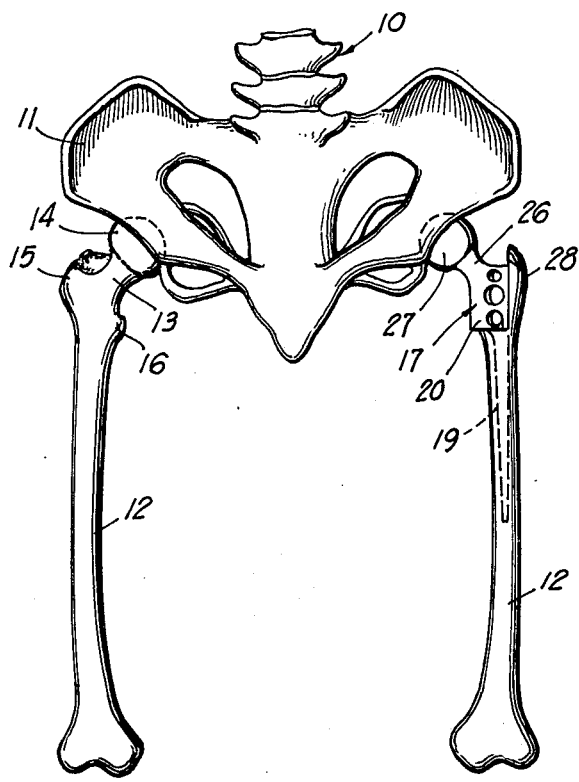
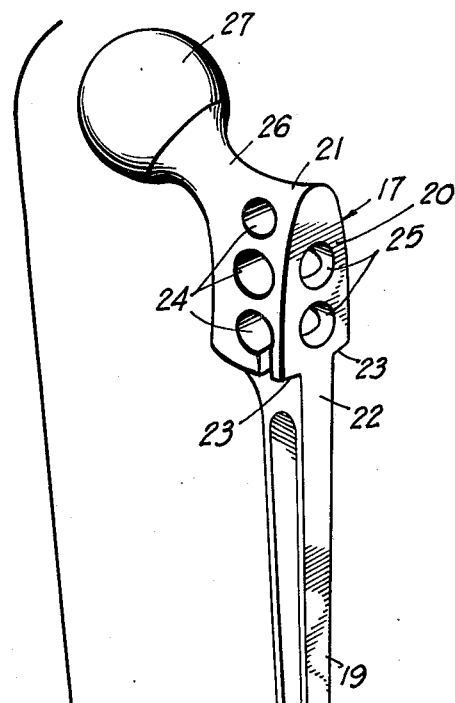
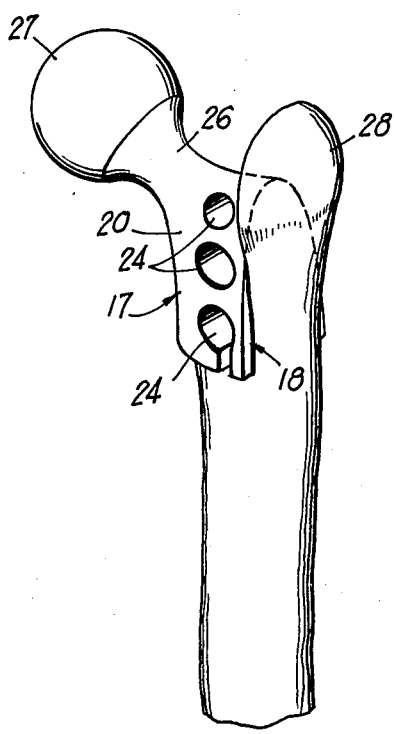
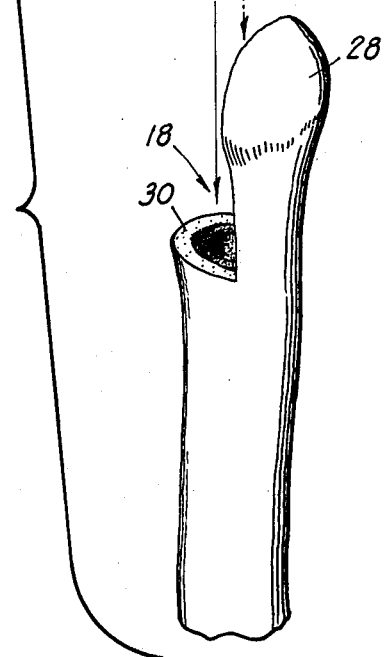
FIG 1
FIG 2
FIG 3

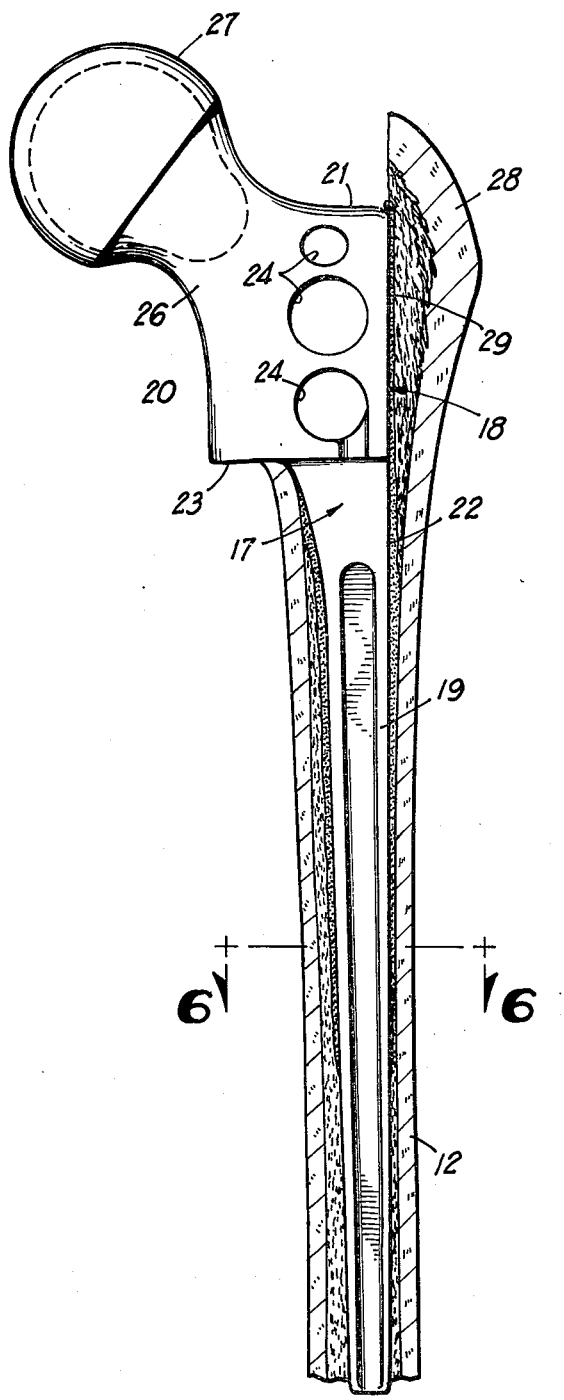
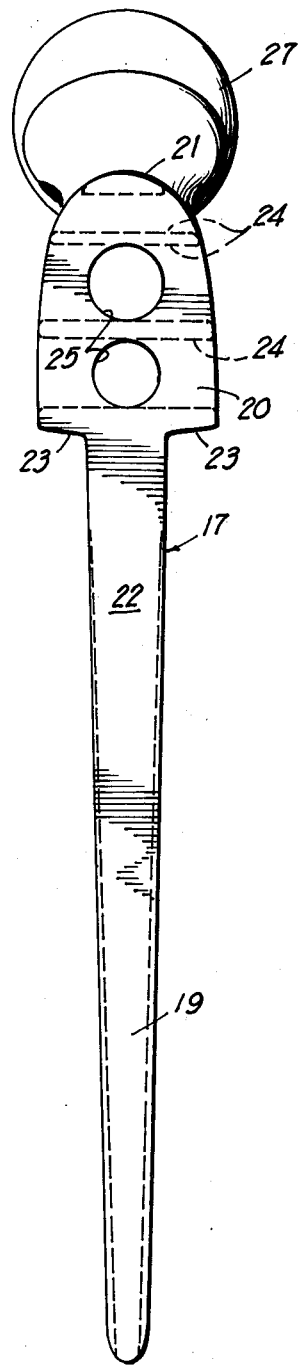
FIG 4   FIG 5
FIG 6

HIP PROSTHESIS

BACKGROUND OF THE INVENTION

Until the present, the customary treatment of comminuted intertrochanteric fractures of the hip has involved open reduction and internal fixation with some sort of nail and plate device. The elderly patient (octagenarian or physiological equivalent) presents special problems where this conventional type of treatment is used. The required six months non-weight bearing period following operation is not only exceedingly difficult when the elderly are ambulated but osteoporosis and other poor quality bone problems allow frequent fixation failures.

Accordingly, the primary objective of the invention is to provide an improved prosthesis to be used in the replacement initially of the comminuted intertrochanteric fracture fragments in the elderly so that very early weight bearing and early ambulation can be achieved. The fear of loss of fixation due to multiple post-operative management problems is precluded by the use of the prosthesis and attendant surgical method embodying the invention.

Other features and advantages of the invention will appear to those skilled in the art during the course of the following detailed description.

Some examples of the known patented prior art are contained in the following U.S. Pat. Nos.: 2,719,522, 3,740,769, 3,320,951, 3,793,650, 3,512,184, 3,814,089, 3,656,184, 3,843,975.

In the prior art, the D'aubigne-Leinbach prosthesis was designed to replace only a small portion of head and neck and has an extremely short neck component making function of a trochanteric fracture replaced hip poor and tending to dislocate the prosthesis. The Austin-Moore prosthesis, as well as other femoral head prostheses such as the Thompson, the Charnley-Mueller prosthesis and Bechtol prosthesis are all designed for the replacement of the femoral neck only and rely upon the greater trochanter being preserved. All of these prostheses, likewise, have been designed for the use in the replacement of fractures of the femoral neck and the replacement of head and short portions of the neck in pathological conditions only, and thus are not suited for the purposes of the invention, where the prosthesis must replace the femoral head, neck and greater and lesser trochanters.

BRIEF DESCRIPTION OF THE DRAWINGS

FIG. 1 is a front elevational view of the pelvis and femoral shafts and showing the hip prosthesis of the invention installed.

FIG. 2 is an exploded perspective view showing the prosthesis prior to insertion in the previously notched femoral shaft.

FIG. 3 is a perspective view showing the prosthesis fully inserted and seated in the femoral shaft.

FIG. 4 is an enlarged longitudinal cross section through the femoral shaft with the improved prosthesis inserted and seated as in FIG. 3.

FIG. 5 is a rear side elevational view of the prosthesis.

FIG. 6 is a transverse section taken on line 6—6 of FIG. 4.

DETAILED DESCRIPTION

Referring to the drawings in detail wherein like numerals designate like parts and initially referring to FIG. 1, the numeral 10 designates the innominate bone including the acetabulum 11. The femur includes a shaft 12, angular neck 13 and femoral head 14 normally engaged for articulation in the cotyloid cavity or socket of the innominate bone. The femur additionally includes the greater trochanter 15 and the lesser trochanter 16 positioned as shown at the left portion of FIG. 1. The right portion of FIG. 1 shows a hip prosthesis 17 embodying the invention installed and seated in the femoral shaft shaft 12 following removal of the femoral head, neck and the greater and lesser trochanters and notching of the femoral shaft at 18 to form a square seat for the prosthesis, as will be further described. The placement of the prosthesis 17 as illustrated in FIG. 1 is for the treatment, particularly in the elderly, of comminuted intertrochanteric fractures of the hip which cannot be satisfactorily treated by the traditional method involving open reduction and internal fixation by means of a nail and plate device, or the like.

Referring now to all figures of the drawings, the prosthesis 17 which is unitary in construction comprises a square I-beam cross section stem 19 which gradually tapers toward its lower end. This stem measures approximately six inches in length. At the top of the stem 19 and integral therewith is an enlarged trochanteric portion 20 which is roughly rectangular, as viewed from the side, although rounded or arched at its top 21 as viewed at right angles to the position of FIG. 4. The trochanteric portion 20 forms with the stem 19 a continuous flat surface 22 for the full length of the stem and the full height of the portion 20 above the stem. At right angles to this flat surface 22, the portion 20 has two base surfaces or shoulders 23 which project laterally and equidistantly beyond opposite sides of the stem 19 for seating purposes, to be further described. The trochanteric portion 20 is preferably provided through its opposite sides with openings 24 and through its rear face with additional openings 25 which intersect the openings 24. These openings in the thick or heavy portion 20 of the prosthesis help in reducing the mass of the molded device and also assist in reanastomosing the abductor musculature and its trochanteric shell of bone. It should be mentioned that the prosthesis 17 is formed from any suitable material that is clinically inert, exhibits minimal foreign body reaction when disposed in living tissue, and is non-electrolytic.

The prosthesis 17 further comprises near its upper end an angular neck portion 26 rising from the trochanteric portion 20 and being approximately one inch in length. The portion 20 measures approximately two inches in length by one and one-eighth inches in width. At its top, the prosthesis has a hollow ball section 27 which is polished and welded to the neck portion 26. The overall length of the prosthesis is nine and one-half inches. The ball or head size varies and is provided preferably in one-eighth increments from a minimum diameter of one and one-half inches to two and one-quarter inches to meet all needs.

The surgical method embodying the invention and utilizing the improved prosthesis 17 can be described as follows. In cases of comminuted intertrochanteric fractures of the hip, the patient's fractured femoral head 14, neck 13 and comminuted trochanteric portion are removed substantially to the inferior border or base of the lesser trochanter 16. In practice, a bone shell or extension 28 is left attached to the gluteal muscles and external rotator muscles. When the extension 28 is fractured from its femoral origin, it can be reattached by securing it with wire to the prosthesis 17. In effect, the femur is provided by the surgeon with a square or right angular notch previously identified at 18 and this square notch forms a solid and stable seat for the flat rear face of the trochanteric portion 20 and its right angular base shoulders 23, as best shown in FIGS. 3 and 4.

The femoral shaft 12 is then reamed according to conventional procedure and a prosthesis 17 of proper head size is selected and its stem 19 is inserted into the canal of the femoral shaft as depicted in FIG. 4. The prosthesis is then reduced into the acetabulum 11 and leg length is checked. The prosthesis seeks a seating angle in the shaft 12 which can only be minimally varied. This angle should be approximately 30-35 degrees anteversion in relation to the patella. When proper fit has been accomplished, the prosthesis is cemented into the femoral shaft with Simplex-P bone cement (methylmethacrylate) or equivalent material. As illustrated in FIG. 4, one cement layer 29 bonds the rear flat surface of the portion 20 to the bone shell 28 in the square notch 18. The base shoulders 23 are additionally bonded with cement to the right angular ledge 30, FIG. 2, of the notch 18 in which the trochanteric portion 20 is seated. The arrangement provides a stable engagement of the prosthesis with the femoral shaft 12 to assure good and permanent fixation of the prosthesis without the drawbacks of the prior art.

The invention allows the patient to place weight on the leg immediately after surgery, whereas, heretofore, up to two to three months of restriction to bed has been necessary and total recuperation time has been as much as six months in cases of intertrochanteric fracture. Additional advantages of the invention over the prior art are that the insertion stem 19 is centrally located with respect to the limits of the prosthesis and is of shorter length. Also, the portion of the prosthesis above the stem 19 and shank ledge 30 is substantially of the configuration which will match the portions of natural bone 13, 14 and 15 which are removed.

It is to be understood that the form of the invention herewith shown and described is to be taken as a preferred example of the same, and that various changes in the shape, size and arrangement of parts may be resorted to, without departing from the spirit of the invention or scope of the subjoined claims.

I claim:

1. A hip prosthesis comprising a trochanteric enlargement having two right angular surfaces forming a flat base and side wall on the enlargement, an angled neck and ball head projecting above and to one side of the trochanteric enlargement, and an elongated stem of comparatively small cross section extending from the base of the trochanteric enlargement and having a flat side face in a common plane with said side wall of the trochanteric enlargement, said enlargement having two additional side walls extending substantially parallel to each other and at right angles to said first side wall, the upper portions of said additional side walls being joined by an arched portion, a plurality of spaced openings extending through said first side wall and a plurality of correspondingly spaced openings extending through each of said additional side walls and intersecting said first openings.

2. A hip prosthesis as in claim 1 wherein the elongated stem has an I-cross section.

3. A hip prosthesis as in claim 1 wherein the openings in said additional side walls are circular in cross section and wherein channels are provided connecting the bottom ones of said openings with the base of the enlargement.

4. A hip prosthesis as in claim 1 wherein the neck is significantly elongated thereby preventing post-operative dislocation.

5. A hip prosthesis as in claim 1 wherein said hip prosthesis serves to replace the entire proximal femur for intertrochanteric fractures.

* * * * *